United States Patent [19]

Van Atta et al.

[11] Patent Number: 5,478,729
[45] Date of Patent: Dec. 26, 1995

[54] IMMUNOASSAY FOR HOMOCYSTEINE

[75] Inventors: Reuel B. Van Atta; Thomas C. Goodman, both of Mountain View; Edwin F. Ullman, Atherton, all of Calif.

[73] Assignee: Syntex (U.S.A.) Inc., Palo Alto, Calif.

[21] Appl. No.: 234,456

[22] Filed: Apr. 28, 1994

[51] Int. Cl.$^6$ .................. G01N 33/546; G01N 33/577
[52] U.S. Cl. .................. 435/7.93; 435/7.5; 435/975; 436/531; 436/815; 436/825
[58] Field of Search .................. 435/7.93, 975, 435/7.5; 436/815, 822, 825, 531

[56] References Cited

U.S. PATENT DOCUMENTS

| | | | |
|---|---|---|---|
| 4,940,658 | 7/1990 | Allen et al. | 436/505 |
| 4,952,336 | 8/1990 | Brynes et al. | 252/301.16 |
| 4,978,632 | 12/1990 | Mach et al. | 435/188 |

FOREIGN PATENT DOCUMENTS

| | | |
|---|---|---|
| 351248 | 1/1990 | European Pat. Off. . |
| WO91/06856 | 5/1991 | WIPO . |
| WO93/01496 | 1/1993 | WIPO . |
| WO93/15220 | 8/1993 | WIPO . |

OTHER PUBLICATIONS

Ueland, et al., Clinical Chemistry, vol. 39(9): 1764–1779 (1993), "Total Homocysteine in Plasma or Serum: Methods and Clinical Applications".

Andersson, et al., Clinical Chemistry, vol. 39(8): 1590–1597 (1993), "Homocysteine and Other Thiols Determined in Plasma by HPLC and Thiol–Specific Postcolumn Derivatization".

Fiskerstrand, et al., Clinical Chemistry, vol. 39(2): 263–271 (1993), "Homocysteine and Other Thiols in Plasma and Urine: Automated Determination and Sample Stability".

Refsum, et al., Clinical Chemistry, vol. 31(4): 624–628 (1985), "Radioenzymic Determination of Homocysteine in Plasma and Urine".

Jue, et al., Analytical Biochemistry, vol. 210: 39–44 (1993), "Identification of Cysteine Residues Alkylated with 3–Bromopropylamine by Protein Sequence Analysis".

*Primary Examiner*—Mary E. Ceperley
*Attorney, Agent, or Firm*—Shelley G. Precivale

[57] ABSTRACT

This invention pertains to methods to detect a compound in the presence of a homolog that is immunologically related to the analyte. The invention is particularly suited for the detection of homocysteine in the presence of cysteine. The methods of this invention involve chemically modifying both the analyte and the homolog to increase their immunogenicity and facilitate antibody recognition. More importantly, this modification is done to make these compounds immunologically distinct. Antibodies to the immunologically distinct compounds are then prepared. An assay protocol comprises chemically modifying the analyte and homolog and then immunochemically detecting the modified analyte by means of the aforementioned antibodies.

29 Claims, No Drawings

IMMUNOASSAY FOR HOMOCYSTEINE

BACKGROUND OF THE INVENTION

1. Field of the Invention

Homocysteine (Hcy) is one in a series of intermediates produced along the transsulfuration pathway in which methionine is eventually converted to cysteine (Cys). The exclusive source of Hcy in mammals derives from the product of the enzyme catalyzed hydrolysis of S-adenosylhomocysteine. Once formed, Hcy may reenter the cycle through remethylation and conversion to methionine or combine with serine to form cystathionine, which is ultimately converted to Cys. The major metabolic pathway for the methylation of Hcy by methionine synthase requires vitamin $B_{12}$ (cobalamine) as a methyl-transfer cofactor and 5-methyl-tetrahydrofolate as the ultimate methyl source. Not surprisingly, elevated levels of serum Hcy have been associated with insufficient intake of vitamin $B_{12}$ or folate, or a deficiency in the ability to properly utilize these two vitamins. Moderately elevated levels of Hcy usually can be brought into balance by administering folate, a treatment for which there are few adverse side-effects.

In addition to anemia, individuals who are heterozygous for a defective cystathionine synthase gene, which results in a 50% diminution of normal enzymatic activity, are particularly susceptible to elevated Hcy levels following methionine loading. This genetic predisposition is the most common cause of moderate homocysteinuria (build-up of Hcy in urine) in otherwise healthy patients.

Lastly, there appears to be a correlation between moderately elevated levels of Hcy and cardiovascular disease.

For these reasons, there has been great interest in developing an accurate Hcy assay.

2. Description of the Related Art

There are several techniques to quantitate total homocysteine (Hcy) as well as distinguish between the free (reduced and disulfide) and protein-bound (primarily albumin) forms.

An excellent overview of the causes of homocysteinuria as well as an update on the current methods of clinical analysis can be found in Ueland, et al., *Clin. Chem.* 39(9):1764–1779 (1993).

An enzymatic method for a Hcy assay is described by Sundrehagen, et al., PCT/GB93/00138, where Hcy is assayed indirectly by measuring the product concentration following the enzyme catalyzed conversion of Hcy to S-adenosyl homocysteine.

High performance liquid chromatographic ("HPLC") methods for Hcy and Cys are known in the art. This analytical method discriminates between Hcy and Cys by differential adsorption and elution of the compounds on a chromatographic support. Andersson, et al., *Clin. Chem.* 39(8):1590–1597 (1993) describes the determination of total, free and reduced Hcy and Cys.

Hcy and Cys analysis by means of a gas chromatograph-mass spectrometer is described in Allen, et al., U.S. Pat. No. 4,940,658. Allen, et al., PCT/US92/05727 describes a chromatographic assay for cystathionine, the intermediary amino acid between Hcy and Cys produced in the metabolism of methionine.

Fiskerstrand, et al., *Clin. Chem.* 39(2):263–271 (1993) describes a fully automated analysis of total Hcy involving fluorescent labeling of serum thiols, followed by chromatographic separation of the Hcy derivative from the other sulfur-containing compounds.

Identification of Hcy by HPLC methods often involves derivatization with fluorescent reagents such as is described in Fiskerstrand, supra or a radioenzymatic technique such as is described in Refsum, et al., *Clin. Chem.* 31(4) 624–628 (1985). In addition, identification of Cys by protein sequence analysis involves derivatization with alkylating reagents. See, for example, Jue, et al., *Analytical Biochemistry* 210:39–44 (1993).

Unfortunately, chromatographic methods have the disadvantage of being slow and labor intensive. Furthermore, current methods of Hcy analysis require prior derivatization with fluorescent labels, such as bromobimane, in which the bromomethyl group reacts with the free thiol of Hcy, thus forming a thioether and releasing free bromide ion. The bromobimane reagent also reacts with all other free thiols in solution, therefore chromatographic separation of the various derivatized sulfur-containing species is necessary.

As many of the current methods of Hcy analysis rely on cumbersome chromatographic techniques, there is a need for a faster and simpler antibody-based assay for Hcy. To date, an immunoassay for Hcy has not been employed, based on the expectation that it would be problematic because the Hcy molecule is likely to be too small and contain too few antibody recognition features to serve as an effective hapten toward antibody development. Furthermore, antibodies may not attain the degree of antigenic specificity required to distinguish between Hcy and Cys, which differ in structure by a single methylene group. Accordingly, there is a present need for the development of an immunoassay method that would permit highly specific quantitation and differentiation of these compounds.

There are numerous techniques for handling undesirable cross-reactants. Brynes et al., U.S. Pat. No. 4,952,336, describes a method of pretreating a sample with an aqueous periodate solution to eliminate cross-reactants in an amphetamine-methamphetamine immunoassay. Stevenson, PCT/GB90/01649, pertains to an improved immunoassay where the level of interference from rheumatoid factor is reduced by pretreating the sample with a reducing agent. Mach, et al., U.S. Pat. No. 4,978,632 pertains to an improved immunoassay where the level of interference from blood and blood products is eliminated by pretreating the sample with an oxidizing agent. These pretreatment methods only affect the cross-reactants; none of the methods affect the analyte.

SUMMARY OF THE INVENTION

The present invention pertains to a method of determining the presence or amount of a first compound in the presence of a second compound in a sample suspected of containing the compounds, wherein the compounds are immunologically related, comprising the steps of (a) bringing together in an aqueous medium: the sample, a modifying reagent capable of chemically modifying the first compound and the second compound to form a modified first compound and a modified second compound, wherein the modified compounds are immunologically distinct, and an antibody capable of specifically binding to the modified first compound but not to the modified second compound to form an immune complex; and (b) measuring the extent of binding of the antibody to the modified first compound, the extent thereof being related to the presence or amount of the first compound in the sample. This method is particularly well suited to an assay for Hcy in the presence of immunologically related Cys.

Another embodiment of the invention pertains to a method for determining the amount of Hcy in the presence of Cys in a sample suspected of containing Hcy, comprising the steps of (a) bringing together in an aqueous medium: the sample, a modifying reagent capable of chemically modifying Hcy and Cys to form modified Hcy and modified Cys, and an antibody capable of specifically binding to the modified Hcy but not to the modified Cys to form an immune complex; and (b) measuring the amount of the immune complex, the amount thereof being related to the amount of Hcy in the sample.

One embodiment of the invention relates to a method of determining the amount of Hcy in the presence of Cys in a sample suspected of containing Hcy, comprising the steps of (a) bringing together in an aqueous medium: the sample, a modifying reagent capable of chemically modifying Hcy and Cys to form modified Hcy and modified Cys, an analog of the modified Hcy bound to a detectable label, and an antibody capable of specifically binding to the modified Hcy and to the analog, but not to the modified Cys and (b) measuring the extent of binding of the analog to the antibody, the extent thereof being related to the amount of Hcy in the sample.

Another embodiment of the invention pertains to a method of determining the amount of Hcy in a sample suspected of containing Hcy and Cys, comprising the steps of (a) bringing together in an aqueous medium: the sample, a modifying reagent capable of chemically modifying Hcy and Cys to form modified Hcy and modified Cys, an antibody capable of specifically binding to the modified Hcy but not to the modified Cys to form an immunecomplex, a surface capable of binding the antibody, and a labeled analog of the modified Hcy; and (b) measuring the extent of binding of the labeled analog to the antibody, the extent thereof being related to the amount of Hcy in the sample.

Still yet another embodiment concerns a method of determining the amount of Hcy in a sample suspected of containing Hcy and Cys comprising the steps of (a) bringing together in an aqueous medium: the sample, a modifying reagent capable of chemically modifying Hcy and Cys to form modified Hcy and modified Cys, an antibody capable of specifically binding to the modified Hcy but not to the modified Cys to form an immunecomplex, and a receptor capable of binding to a portion of the modifying reagent, wherein the portion is present on the modified Hcy; and (b) measuring the extent. of binding of the antibody to the receptor, the extent thereof being related to the amount of Hcy in the sample.

Yet another embodiment pertains to method of determining the amount of Hcy in the presence of Cys in a serum sample suspected of containing Hcy wherein at least a portion of Hcy is in the disulfide form (protein-bound and free-disulfide), comprising the steps of (a) bringing together in an aqueous medium: the sample, a releasing agent to release Hcy from the disulfide form, a modifying reagent capable of chemically modifying the sulfhydryl groups of Hcy and Cys to form modified Hcy and modified Cys, and an antibody capable of specifically binding to the modified Hcy but not to the modified Cys to form an immunecomplex; and (b) examining the medium for the amount of the immunecomplex, the amount thereof being related to the amount of Hcy in the sample.

Another embodiment of the invention relates to a kit for use in a method for detecting Hcy, comprising in a packaged combination: a modifying reagent capable of chemically modifying Hcy and Cys to form modified Hcy and modified Cys, and an antibody capable of specifically binding to the modified Hcy but not to the modified Cys. The kit may also comprise a labeled analog of the modified Hcy and a releasing agent.

DESCRIPTION OF THE SPECIFIC EMBODIMENTS

This invention pertains to methods to detect a compound in the presence of a homolog that is immunologically related to the analyte. The methods of this invention involve chemically modifying both the analyte and the homolog to increase their immunogenicity and facilitate antibody recognition. More importantly, this modification is done to make these compounds immunologically distinct. The chemical modification preferably comprises more than replacement of a hydrogen by a chemical group. Antibodies to the modified and immunologically distinct compounds are then prepared. An assay protocol comprises chemically modifying the analyte and homolog and then immunochemically detecting the modified analyte by means of the aforementioned antibodies. In particular, this invention relates to quantitative immunochemical methods that discriminate between the sulfhydryl amino acids homocysteine (Hcy) and cysteine (Cys). Hcy and Cys are homologs:

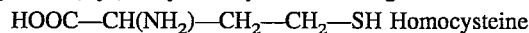

HOOC—CH(NH$_2$)—CH$_2$—CH$_2$—SH Homocysteine

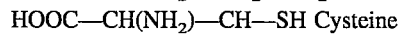

HOOC—CH(NH$_2$)—CH—SH Cysteine

Furthermore, Hcy and Cys are immunologically related because an antibody generated against Hcy would be expected to crossreact with Cys, as there is only a single carbon difference between the two compounds in the length of their amino acid side chains.

Before proceeding further with the description of the specific embodiments of the present invention, a number of terms will be defined.

Analyte: The compound or composition to be detected. The analyte can be a member of a specific binding pair ("sbp") and may be a ligand, which is monovalent (monoepitopic) or polyvalent (polyepitopic), usually antigenic or haptenic, and is a single compound or plurality of compounds which share at least one common epitopic or determinant site.

This invention provides a method to detect an analyte in a sample that also contains a homolog of the analyte, by chemically modifying the analyte and the homolog, then detecting the modified analyte. Therefore, the analyte is determined by detecting a reaction product whose presence will be detected only when the analyte of interest is present in the sample. Thus, the "modified" analyte is actually detected in the assay. The analyte can be found directly in a sample such as a body fluid from a host, for example, urine, blood, plasma, serum, saliva, semen, stool, sputum, cerebral spinal fluid, tears, mucus, or the like, but preferably is serum or plasma. The sample may be pretreated, as discussed below.

Member of a specific binding pair ("sbp" member): one of two different molecules, having an area on the surface or in a cavity that specifically binds to and is therefore defined as complementary with a particular spatial and polar organization of the other molecule. The members of the sbp can be referred to as ligand and receptor such as members of an immunological pair, e.g., antigen-antibody. As used herein, the term "ligand" refers to any compound for which a receptor naturally exists or can be prepared and the term "receptor" refers to any compound or composition capable of recognizing a particular spatial and polar organization of a molecule, i.e., epitopic or determinant site. Complementary sbp members bind to one another, as for example, a ligand and its complementary receptor. Sbp members can be immunological pairs such as antigen and antibody, or non-immunological such as avidin and biotin or the complementary strands of an oligonucleotide. Sbp members can also be small molecules or residues of small molecules and their receptors. Small molecules have a molecular weight of from 100 to 2000, preferably 150 to 1000, and either a receptor exists or can be prepared. Examples of small molecules include derivatives of biotin, lysergic acid, fluorescein or a fluorescein derivative, and vitamin $B_{12}$, with the corresponding receptors being avidin or streptavidin, anti-lysergic acid, anti-fluorescein and intrinsic factor, respectively. Antibodies to small molecules can be prepared by linking the small molecule to an immunogenic carrier.

Support or surface: The solid phase is typically a support or surface, which is a porous or non-porous water insoluble material that can have any one of a number of shapes, such as strip, rod, particle, including beads and the like. Suitable materials are well known in the art and are described in, for example, Ullman, et al. U.S. Pat. No. 5,185,243, columns 10–11, which is incorporated herein by reference. Binding of sbp members to the support or surface may be accomplished by well-known techniques, commonly available in the literature. See, for example, "Immobilized Enzymes," Ichiro Chibata, Halsted Press, New York (1978) and Cuatrecasas, *J. Biol. Chem.* 245:3059 (1970).

Whatever type of solid support is used, it must be treated so as to have antibodies that specifically bind the modified analyte bound to its surface or a receptor bound to its surface, which receptor will specifically bind to such antibodies or to a small molecule conjugated to such antibodies. For example, avidin or streptavidin can be covalently bound to spherical glass beads of 0.5–1.5 mm and used to capture a biotinylated antibody.

Signal producing system ("sps"): one or more components, at least one component being a label, which generate a detectable signal that relates to the amount of bound and/or unbound label. Preferably, the label is a fluorescer, radiolabel, enzyme, chemi-luminescer or photosensitizer, which are detected by observing enzyme activity, luminescence, light absorbance or radioactivity.

Suitable labels include, by way of illustration and not limitation, enzymes such as alkaline phosphatase and horseradish peroxidase; a substrate for a replicase such as QB replicase; promoters; dyes; fluorescers, such as fluorescein, isothiocyanate, rhodamine compounds, phycoerythrin, phycocyanin, allophycocyanin, o-phthaldehyde, and fluorescamine; chemiluminescers such as isoluminol; sensitizers; coenzymes; enzyme substrates; radiolabels such as $^{125}I$, $^{131}I$, $^{14}C$, $^{3}H$, $^{32}P$ and $^{35}S$; particles such as latex or carbon particles; metal sol; crystallite; liposomes; cells, etc., which may or may not be further labeled with a dye, catalyst or other detectable group and the like. Suitable enzymes and coenzymes are disclosed in Litman, et al., U.S. Pat. No. 4,275,149, columns 19 to 28, and Boguslaski, et al., U.S. Pat. No. 4,318,980, columns 10 to 14; suitable fluorescers and chemiluminescers are disclosed in Litman, et al., U.S. Pat. No. 4,275,149, at columns 30 and 31; which disclosures are all incorporated herein by reference.

There are numerous methods by which the label can produce a signal detectable by external means, such as visual examination, electromagnetic radiation, electrochemical detection, phonaccoustic spectroscopy, and the like. The label or other sps members can also be bound to an sbp member, another molecule or to a support.

The label can directly produce a signal, and therefore, additional components are! not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. Other labels that directly produce a signal include radioactive isotopes and dyes.

Alternately, the label may need other components to produce a signal, and the sps would then include all the components required to produce a measurable signal, which may include substrates, coenzymes, enhancers, additional enzymes, substances that react with enzymic products, catalysts, activators, cofactors, inhibitors, scavengers, metal ions, specific binding substance required for binding of signal generating substances, and the like. A detailed discussion of suitable signal producing systems can be found in Ullman, et al. U.S. Pat. No. 5,185,243, columns 11–13, which is incorporated herein by reference.

The label can be bound covalently to numerous sbp members: an antibody that binds the modified analyte; a receptor for an antibody that binds the modified analyte; a receptor that is capable of binding to a small molecule conjugated to an antibody that binds the modified analyte; or a ligand, particularly an analog of the modified analyte. Bonding of the label to the sbp member may be accomplished by chemical reactions which result in replacing a hydrogen atom of the label with a bond to the sbp member or may include a linking group between the label and the sbp member. Other sps members may also be bound covalently to sbp members. For example, two sps members such as a fluorescer and quencher can be bound respectively to an analog of the modified analyte and an antibody to the analyte that forms a complex with the analog. Formation of the complex brings the fluorescer and quencher in close proximity, thus permitting the quencher to interact with the fluorescer to produce a signal. Methods of conjugation are well known in the art. See for example, Rubenstein, et al., U.S. Pat. No. 3,817,837, which is incorporated herein by reference. This invention also contemplates having an antibody bound to a first member of a signal producing system and a detectable label as the second member of a signal producing system. For example, when the detectable label is bound to an analyte analog, the extent of binding of the antibody to the analog can be measured by detecting the signal produced by thee interaction of the signal producing system members.

Ancillary Materials: Various ancillary materials will frequently be employed in the methods in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, or surfactants, particularly non-ionic surfactants, binding enhancers, e.g., polyalkylene glycols, or the like.

As mentioned above, this invention pertains to methods to detect a compound in the presence of a homolog that is immunologically related to the analyte.

One method of the present invention pertains to the determination of the presence or amount of a first compound in the presence of a second compound in a sample suspected of containing the compounds, wherein the compounds are immunologically related. The method comprises the steps of (a) bringing together in an aqueous medium: the sample, a modifying reagent capable of chemically modifying the first compound and the second compound to form a modified first compound and a modified second compound, and an antibody capable of specifically binding to the modified first compound but not to the modified second compound to form an immunecomplex; and (b) measuring the extent of binding of the antibody to the modified first compound, the extent thereof being related to the presence or amount of the first compound in the sample. This method is particularly useful when the compounds are homologous.

As used herein the term "immunologically related" is used to refer to two compounds, one of which is the analyte of interest, for which an antibody exists that exhibits cross-reactivity. Calculation of the cross-reactivity is based upon the ratio of the concentrations of the two compounds that result in equal binding to the antibody. Antibodies to different homologs often display high cross-reactivity. Frequently, therefore, a compound can not be accurately measured in an immunoassay if a homolog is present in the medium. In that case, using an antibody reagent to detect the analyte, may often result in some of the antibodies binding to the homolog and giving a false positive or an inaccurate quantitative reading. The extent of cross-reactivity that is acceptable in an immunoassay depends upon the highest concentration expected of the cross-reactant, the sensitivity required for the assay and the accuracy needed. For example, if an antibody is 10% cross-reactive with Cys and Cys is present in a sample five times greater than the lowest level of Hcy to be detected, then the measured level of Hcy will be 50% too high when Hcy is at its lowest level. If only a 5% error is acceptable, then the cross-reactivity would have to be less than 1%. In the present invention, antibodies directed against the modified analyte must exhibit a low degree of cross-reactivity with the modified homolog. As exemplified above, quantification of a "high" or "low" degree of cross-reactivity will depend upon the maximum expected concentration of the modified homolog and the sensitivity and accuracy desired.

As used herein, the term "homologous" describes a compound in a series of organic compounds that have the same chemical functional groups, and which differ from the next by an insertion of a —$CH_2$— group in the molecule. For example, $CH_3OH$ (methanol), $C_2H_5OH$ (ethanol) and $C_3H_7OH$ (propanol), etc., are all homologs and form a homologous series. Examples of homologous compounds within the scope of this invention are homocysteine and cysteine, amphetamine and methamphetamine, serine and homoserine, citrate and homocitrate, aspartate and glutamate, alanine and β-amino-isobutyrate, tetrahydrofolate and $N^5$-methyltetrahydrofolate, oxaloacetate and α-ketoglutarate, gentisic acid and homogentisic acid, morphine and normorphine, and the like.

As used herein the term "modifying reagent" is used to mean a reagent that reacts with two homologs to form two new and immunologically distinct compounds. The term "immunologically distinct" means that antibodies to the immodified analyte are available that exhibit low cross-reactivity with the modified homolog. Homologs have the same functional groups, and antibodies to different homologs often display a high degree of cross-reactivity. Therefore a compound can not be accurately measured in an immunoassay if a homolog is present in the medium. The modifying reagent is capable of chemically modifying the compound being assayed (the "analyte") and its homolog so that the two compounds become immunologically distinct. As a result, antibodies to the modified analyte exhibit lower cross-reactivity with the modified homolog. The modifying reagent will usually be soluble in aqueous solvents. The modifying reagent is selected so that it will modify both compounds, within a short time, usually less than 4 hours, preferably less than 20 minutes, and most preferably less than 5 minutes. It must be used in sufficient quantities that if it reacts with other components in the sample, it will be available to react with the analyte. Examples of suitable modifying reagents include alkylating agents, acylating agents, metals, nucleophiles and electrophiles. This invention also contemplates having a modifying reagent with a detectable label bound to it, such as a radiolabel. In that instance, the amount of modified analyte can then be measured by detecting the label.

In the above described method for detecting a first compound in the presence of a second, immunologically related compound, the antibody can be detectably labeled or be capable of being detectably labeled. Alternatively, when the modifying reagent is labeled, the antibody can be bound to a support or can be capable of being bound to a support.

As used herein, the terms "capable of being detectably labeled" and "capable of being bound to a support" means that a reagent, such as the antibody in this instance, is bound to a first sbp member or a small molecule and a complementary second sbp member or receptor for the small molecule, is in turn bound to a label or a support. Therefore, the antibody is not actually labeled or bound to a support, but will become labeled or bound, when the complementary sbp member or receptor is added.

The method described above can further comprise bringing together an analog of the modified first compound bound or capable of being bound to a detectable label and an antibody that can specifically bind both the analog and the modified first compound. The extent of binding of the antibody to the modified first compound is measured by measuring the extent of binding of the analog to the antibody. The antibody can be bound to a support or capable of being bound to a support.

More particularly, this invention involves chemically modifying Hcy and Cys in a sample in a manner that causes them to be immunologically distinct, and then detecting Hcy. One method of determining the amount of Hcy in the presence of Cys in a sample suspected of containing Hcy, comprises the steps of (a) bringing together in an aqueous medium: the sample, a modifying reagent capable of chemically modifying Hcy and Cys to form modified Hcy and modified Cys, and an antibody capable of specifically binding to the modified Hcy but not to the modified Cys to form an immunecomplex; and (b) measuring the amount of the immunecomplex, the amount thereof being related to the amount of Hcy in the sample.

As used herein the term "immunecomplex" means the complex formed by the immunological binding of an antigen to an antibody.

The same labeled reagents are suitable for use in this method as those described above with reference to a method of detecting one compound in the presence of an immunologically related compound, i.e., labeled modifying reagent, labeled antibody, and labeled analog.

In one embodiment of the invention, the modifying reagent is designed to form a bond to at least one of the three functionalities of Hcy and Cys, the amino, sulfhydryl and carboxyl groups. Usually in at least one of the products, a second bond will form to one of these groups after formation of the first bond. This will frequently produce a ring. For example, the first bond can be to the sulfhydryl group and the second bond can involve the amine.

Modifying reagents capable of reacting with the sulfhydryl group of Hcy and Cys usually have a group that is suitably positioned to react with the Hcy or Cys amino or carboxyl groups. This group may be, by way of illustration and not limitation, an alkylating or acylating group, a metal, or an aryl group activated for nucleophilic substitution. Particularly suitable are ketones substituted at the alpha position by a leaving group selected from the group consisting of Cl, Br, I, sulfonates, and sulfonium salts.

As indicated above, alkylating agents, acylating agents and metals are particularly suited as modifying reagents for use in an Hcy assay. As used herein the term "alkylating agent" means a modifying reagent that reacts with an organic molecule to introduce an alkyl or aryl group into the molecule. An alkyl group is a group derived from an alkane by dropping one hydrogen from the formula. For example, methyl, ethyl, propyl, etc. An aryl group is a group whose molecules have the ring structure characteristic of benzene, naphthalene, phenanthrene, anthracene, etc., i.e., either the six-carbon ring of benzene or the condensed six-carbon rings of the other aromatic derivatives. Preferably, the alkylating agent has a group such as an alkyl halide or an aryl halide or electronegatively substituted olefins such as a maleimide or acrylonitrile. When an alkyl halide is used, a ketone, aldehyde, ester, olefin, acetylene, nitrile, aryl, or the like will usually be adjacent to the carbon bearing the halogen. Suitable alkylating agents include, by way of illustration and not limitation, Modifying Reagents I–VIII, shown in the table below. A particularly useful alkylating agent is p-bromoacetylbenzoic acid (BABA), Modifying Reagent II.

AS used herein the term "acylating agent" means a modifying reagent, usually a sulfonic acid or carboxylic acid derivative such as its anhydride or chloride or active ester, that reacts with an organic molecule to introduce a sulfonyl or acyl group into the molecule. An acyl group is an organic acid group in which the —OH of the carboxyl group is replaced by some other substituent. For example, acetyl ($CH_3CO-$) and benzoyl ($C_6H_5CO-$). Suitable acylating agents include, by way of illustration and not limitation, Modifying Reagents III–V and VIII, shown in the table below. As used herein the term "metal" means heavy metal chelates, including organometallic reagents hat are capable of forming chelates with bidentate ligands. Suitable metals include, by way of illustration and not limitation, Modifying Reagents IX and X, shown in the table below.

Particularly useful modifying reagents have an alkylating group such as an alkyl halide or an aryl halide. When an alkyl halide is used, a ketone, aldehyde, ester, olefin, acetylene, nitrile, aryl, or the like will usually be adjacent to the carbon bearing the halogen. Typical reagents and their reaction products with Hcy and Cys, i.e., the "modified" Hcy and Cys, are given in the table below:

| MODIFYING REAGENT | MODIFIED CYSTEINE | MODIFIED HOMOCYSTEINE |
|---|---|---|
| 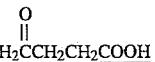 (I) | 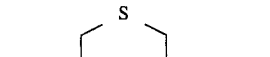 (Ia) | 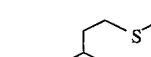 (Ib) |
| 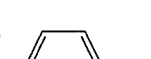 (II) | 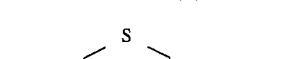 (IIa) |  (IIb) |
| 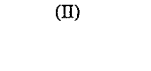 (III) | 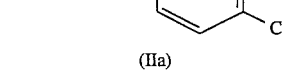 (IIIa) | 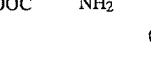 (IIIb) |
|  (IV) | 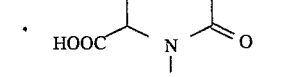 (IVa) | 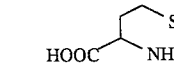 (IVb) |

-continued
| MODIFYING REAGENT | MODIFIED CYSTEINE | MODIFIED HOMOCYSTEINE |
|---|---|---|
| 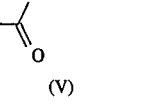 (V) | 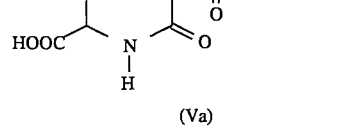 (Va) | 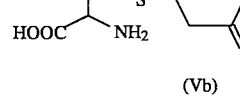 (Vb) |
| 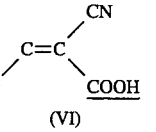 (VI) | 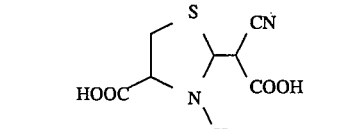 (VIa) | 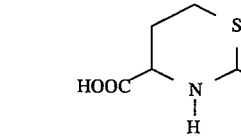 (VIb) |
| 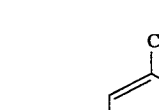 (VII) | 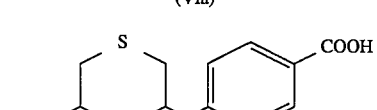 (VIIa) | 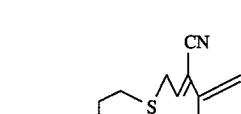 (VIIb) |
| 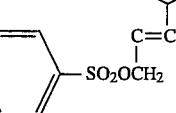 (VIII) | 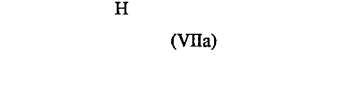 (VIIIa) |  (VIIIb) |
| 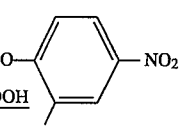 (IX) | 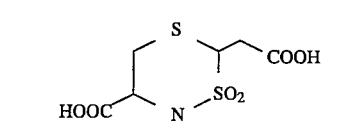 (IXa) | 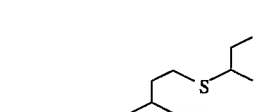 (IXb) |
| 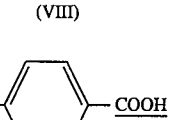 (X) | 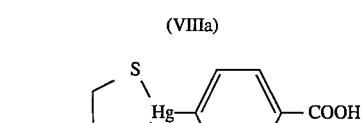 (Xa) | 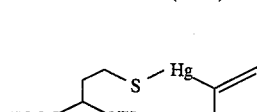 (Xb) |
The underlined group in each reagent is exemplary of a solubilizing group that is not necessary for the derivatization reaction:

| Reagent | Solubilizing Group |
|---------|-------------------|
| I       | —COOH            |
| II      | —COOH            |
| III     | —COOH            |
| IV      | —SO$_3$H         |
| V       | —SO$_3$H         |
| VI      | —COOH            |
| VII     | —COOH            |
| VII     | —COOH            |
| IX      | —COOH            |
| X       | —COOH            |

When a label is present in the modifying reagent, it may as a matter of convenience, be attached through the solubilizing group by means of an amide or ester bond. Preferably, the modifying reagent modifies the sulfhydryl groups of the Hcy and the Cys to form a modified Hcy and Cys where the sulfur of at least one of the modified compounds is part of a ring. Exemplary of modifying reagents where one of the modified compounds forms a ring are Modifying Reagents I–X, shown above. More preferably, a modifying reagent is selected so that both the resulting modified Hcy and Cys have a ring, as is the case with Modifying Reagents VI and X.

Of the aforementioned modifying reagents, a preferred reagent is BABA (Modifying Reagent II), which reacts rapidly with both Hcy and Cys at room temperature and neutral pH. BABA has the following advantages: the phenyl ring provides a highly immunogenic moiety when presented to an immune system; the carboxylate provides some degree of water solubility as well as a convenient point of attachment to a carrier protein; and the carbonyl of the bromoacetyl group provides a convenient means of differentiating between modified Hcy and Cys.

As mentioned above, antibodies to Hcy potentially exhibit a high degree of cross-reactivity with Cys, because Hcy and Cys are homologs and are immunologically related. There are numerous ways to modify Hcy and Cys to make them immunologically distinct. For example, a six-membered ring is stereochemically quite different from a chain and therefore antibody recognition can be improved and cross-reactivity reduced when Cys is modified to form a six-membered ring and the modified Hcy is acyclic. This is illustrated with Modifying Reagent (VIII):

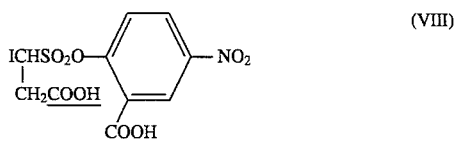

(VIII)

which modifies Cys and Hcy to form Modified Cys (VIIIa), where the sulfur is part of a six-membered ring:

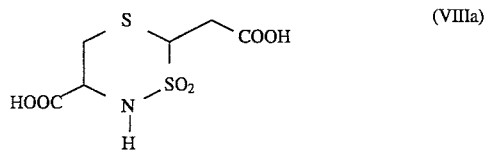

(VIIIa)

and Modified Hcy (VIIIb), where the sulfur is not part of a ring:

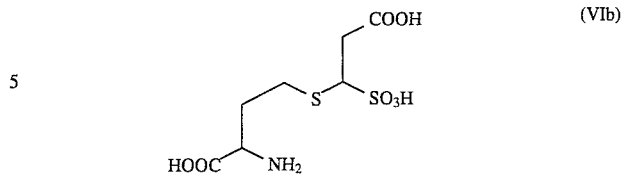

(VIb)

Another embodiment of this invention involves an assay for determining the amount of Hcy in the presence of Cys in a sample suspected of containing Hcy, using the following method: (a) bringing together in an aqueous medium: the sample, a modifying reagent capable of chemically modifying Hcy and Cys to form modified Hcy and modified Cys, an analog of the modified Hcy bound to a detectable label, and an antibody capable of specifically binding to the modified Hcy and to the analog, but not to the modified Cys; and (b) measuring the extent of binding of the analog to the antibody, the extent thereof being related to the amount of Hcy in the sample. In this embodiment, the signal measured is indicative of the extent of binding of the analog to the antibody. Hence the signal is inversely related to the amount of Hcy in the sample.

Still another embodiment of this invention involves an assay for the amount of Hcy in a sample suspected of containing Hcy and Cys, using the following method: (a) bringing together in an aqueous medium: the sample, a modifying reagent capable of chemically modifying Hcy and Cys to form modified Hcy and modified Cys, an antibody capable of specifically binding to the modified Hcy but not to the modified Cys to form an immunecomplex, a surface capable of binding the antibody, and a labeled analog of the modified Hcy; and (b) measuring the extent of binding of the labeled analog to the antibody, the extent thereof being related to the amount of Hcy in the sample. The method can further comprise bringing together a labeled first specific binding pair member, wherein the label of the labeled analog is a complementary second specific binding pair member, for example an analog bound to fluorescein and an enzyme-labeled anti-fluorescein antibody. In this embodiment, the signal measured is indicative of the extent of binding of the analog to the antibody. Hence the signal is inversely related to the amount of Hcy in the sample.

Yet another embodiment of the invention relates to an assay for determining the amount of Hcy in a sample suspected of containing Hcy and Cys, comprising the steps of (a) bringing together in an aqueous medium: the sample, a modifying reagent capable of chemically modifying Hcy and Cys to form modified Hcy and modified Cys, an antibody capable of specifically binding to the modified Hcy but not to the modified Cys to form an immunecomplex, and a receptor capable of binding to a portion of the modifying reagent, wherein the portion is present on the modified Hcy; and measuring the extent of binding of the antibody to the receptor, the extent thereof being related to the amount of Hcy in the sample. The modifying reagent may be comprised of a hapten, a ligand, or a Hcy or Cys receptor, wherein the receptor that binds a portion of the modifying reagent may be an anti-hapten antibody, a receptor for the ligand, or an antibody to the Hcy or Cys receptor, respectively. Either or both the receptor and the specific antibody can be labeled, and one can be bound to a support. The following are merely illustrative of the embodiment encompassed by this method. For example, a modifying reagent bound to biotin forms a modified Hcy bound to biotin. A complex is formed that comprises the modified Hcy, a labeled antibody capable of specifically binding to the modified Hcy and avidin bound to a support. Alternatively, a modifying reagent bound to a hapten forms a modified Hcy bound to the hapten. A complex is formed that comprises the modified Hcy, an antibody capable of specifically binding to the modified Hcy bound to a first label and an anti-hapten antibody bound to a second label.

Hcy exists in human plasma as various mixed disulfides. Normally, a major fraction of Hcy (approximately 70%) is protein bound, via a disulfide bond to circulating proteins such as albumin. The remaining "free" Hcy (approximately 30%) is in the form of Hcy (reduced) or as mixed disulfides with other thiols such as Cys. The sum of these Hcy species present in plasma (protein-bound, free-disulfide and free-reduced) is referred to as the "total Hcy". Measurement of total Hcy in serum, preferably involves a pretreatment step to release protein-bound Hcy and reduce the mixed disulfide form of Hcy, i.e., the free-disulfide form. The preferred method of this invention measures the total Hcy since the ratio of the three forms of Hcy (protein-bound, free-disulfide or free-reduced) is dependent on factors such as Hcy concentration, sample preparation, storage method, etc. However, measurement of free Hcy may be done without pretreatment, if desired.

To measure the total amount of Hcy in a sample, the sample is first combined with a releasing agent to release the Hcy from the circulating proteins as well as from Hcy dimers and other mixed disulfides. Particularly suitable is a reducing agent, which reduces organic disulfides. One such method of determining the amount of Hcy in the presence of Cys in a serum sample suspected of containing the Hcy, wherein at least a portion of the Hcy is in the disulfide form (protein-bound and free-disulfide), comprises the steps of (a) bringing together in an aqueous medium: the sample, a releasing agent to release the Hcy from the disulfide form, a modifying reagent capable of chemically modifying the sulfhydryl groups of Hcy and Cys to form modified Hcy and modified Cys, and an antibody capable of specifically binding to the modified Hcy but not to the modified Cys to form an immunecomplex; and (b) examining the medium for the amount of the immunecomplex, the amount thereof being related to the amount of Hcy in the sample. The releasing agent can be a reducing agent, such as described above, or it could react with disulfides to form modified Hcy and modified Cys and thereby act as both a releasing agent and the modifying reagent.

Suitable releasing agents capable of liberating the Hcy and Cys sulfur compounds from serum proteins are well known in the art and include, without limitation, reducing agents such as sodium and potassium borohydride; thiols such as dithiothreitol, dithioerythritol, 2-mercaptoethanol, thioglycolic acid and glutathione; and phosphines and trialkylphosphines such as tributylphosphine and tris(2-carboxyethyl)phosphine. Particularly suitable reducing agents are dithiothreitol and tris(2-carboxyethyl)phosphine (TCEP), the latter of which is described in Burns, et al., *J. Org. Chem.* 56(8):2648–2650 (1991). The reduction reaction is illustrated below with TCEP, where protein-bound HCy and protein-bound Cys are liberated from the serum protein:

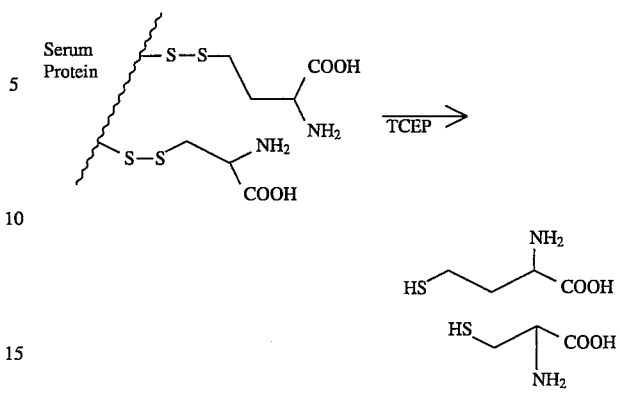

When the releasing agent also acts as a modifying reagent, sulfites, phosphites, phosphorimidates, and the like, including salts of their mono- and di-esters can be used. These reagents react with Hcy and Cys disulfides to give modified Hcy and Cys that have thiosulfate or thiophosphate groups.

On the other hand, when the releasing agent does not act as a modifying reagent, the liberated thiols are modified with a thiol-specific modifying reagent. Selection of the releasing agent may often be determined by the selection of the modifying reagent, as some combinations of reagents are more preferred than others. Many combinations of releasing agents and modifying reagents will react with each other, thus necessitating that the sample and the releasing agent first be combined and then sufficient modifying reagent added to react with the releasing agent and the liberated Hey and Cys. Alternatively, a releasing agent such as a phosphine can be used with an unsaturated modifying reagent such as a maleimide with which it will not react. While this provides more flexibility in the protocol, the use of a less reactive modifying reagent can require a longer incubation period to assure complete reaction with the Hey and Cys. Thus, selection of the releasing agent and modifying reagent will be based upon the desired protocol and timing of the assay.

Appropriate reaction conditions are chosen for carrying out the methods in accordance with the present invention. The following description sets forth suitable conditions, which are subject to modification by those skilled in the art depending on the specific reagents and assay protocol chosen for any particular application. For example, the methods of this invention can be applied to numerous types of assays such as heterogeneous or homogeneous, competitive or direct, and the conditions and reagents used will be selected accordingly.

The sample, preferably in a suitable medium, can be examined directly or may be pretreated before the sample is added to the assay medium. Pretreatment can render the analyte more readily available to one or more of the assay reagents or more readily detectible by reducing interference in the assay by removing any unwanted materials. The sample may be pretreated to separate or lyse cells; precipitate, hydrolyse or denature proteins; hydrolyze lipids; solubilize the analyte; or the like. Such pretreatment may include, without limitation: centrifugation; treatment of the sample with an organic solvent, for example, an alcohol, preferably an alcohol having less than about 7 carbon atoms such as methanol; treatment with detergents; and treatment with a releasing agent.

The concentration of the compound to be assayed will generally vary from about $10^{-4}$ to $10^{-15}$M, more usually from about $10^{-5}$ to $10^{12}$M. More specifically, for an Hcy analyte, the concentration will generally vary from about $10^{-4}$ to $10^{-8}$M, more usually from about $10^{-5}$ to $10^{-7}$M. Considerations such as whether the assay is qualitative, semi-quantitative or quantitative, the particular detection technique, and the concentration of the analyte will normally determine the concentration of the other reagents. In addition, the final concentration of each of the reagents will normally be determined empirically to optimize the sensitivity of the assay over the range of interest.

The relative amounts of the various reagents used in the assay and packaged in the kits described below, can be varied widely to provide for concentrations of the reagents that substantially optimize the reactions that need to occur during the present method and to further substantially optimize the sensitivity of any assay performed. The concentration of the antibodies in the assay medium is dependent on the type of assay, heterogeneous or homogeneous, competitive or direct, etc. Normally, the anti-modified analyte antibody will be present in the assay medium in a concentration of about half to $10^7$ times the concentration of the modified analyte, more usually from about equal to about $10^3$ times the concentration of the modified analyte.

In carrying out the method of this invention, preferably an aqueous medium will be employed. Other polar cosolvents may also be employed in the medium, usually oxygenated organic solvents of from 1–6, more usually from 1–4 carbon atoms, including alcohols, ethers and the like. Usually these cosolvents will be present in less than about 70 weight percent, more usually, in less than about 30 weight percent.

In assays in accordance with the present invention, the pH for the medium will usually be in the range of about 5–10, preferably, in the range of about 7–9. The pH is chosen so as to maintain a significant level of binding between sbp members, while optimizing signal producing proficiency. In some instances, a compromise will be made between these two considerations. In addition, the pH may also be selected so as to maintain a particular structural conformation such as cyclization. Various buffers may be used to achieve the desired pH and maintain the pH during the determination. Illustrative buffers include borate, phosphate, carbonate, Tris, barbital and the like. The particular buffer employed is not critical to this invention but in individual assays, one buffer may be preferred over another.

Moderate temperatures are normally employed for carrying out the method. The temperature may vary with the step being undertaken. More typically, however, a constant temperature is maintained during the period of the method. The temperatures will generally range from 10° to 50° C., usually from about 15° to 40° C.

While the order of addition of the various reagents may be varied widely, there will be certain preferences depending on the nature of the particular assay format being used. The reagents and sample can be combined simultaneously or wholly or partially sequentially with each other and the support. As used herein, the term "wholly or partially sequentially" means that, when the sample and various reagents utilized in the present invention are combined other than concomitantly (simultaneously), one or more of the reagents may subsequently be added alone, or together with other reagents. For example, the sample suspected of containing the analyte and the releasing agent may be combined first to, allow the releasing agent to reduce any disulfide bonds, followed by the simultaneous or stepwise addition of the remaining reagents. Except when the releasing agent and the modifying reagent do not react together, addition of the releasing agent prior to the modifying reagent is preferred. Optionally, one or more incubation steps may be involved after each reagent addition, generally ranging from about 30 seconds to 6 hours, more usually from about 2 minutes to 1 hour. It is understood that there are certain sequences of steps that are more convenient and the choice of the particular sequence to be employed depends upon the selection of reagents and assay format and is not critical to the invention.

The final step of an immunoassay is to measure the extent of binding between the modified analyte and the antibody, which is related to the presence or amount of the analyte in the sample. There are numerous ways to measure the extent of binding which are well known in the art. These methods differ depending on, for example, whether the assay is competitive, homogeneous, heterogeneous, etc.

One measurement of the extent of binding between the modified analyte and the antibody can be accomplished by adding detectably labeled modified analyte, i.e., a labeled analyte analog, and detecting the signal produced by binding of the labeled modified analyte with the antibody in competition with binding of the modified analyte. For example, in a homogeneous assay, the detectable label can be an enzyme and the final step might involve activating the enzyme label by addition of substrate. The signal produced is usually inversely related to the extent of binding between the labeled modified analyte and the antibody. The presence or amount of signal is then related to the presence or amount of analyte in the sample.

In another measurement in a homogeneous assay which is competitive, the extent of binding can be determined by use of a fluorescer-labeled modified analyte and a quencher-labeled antibody. The signal is again inversely related to the extent of binding and directly related to the amount of analyte present in the sample. Alternatively, a homogeneous non-competitive assay may be used in which the fluorescer-labeled modified analyte is not added as a separate reagent but is formed by reaction of the analyte with a fluorescer-labeled modifying reagent. In this case, the signal is again inversely related to the extent of binding, but is inversely related to the amount of analyte present in the sample.

In a heterogeneous assay, unlabeled anti-modified analyte antibodies may be bound to a support. Following incubation of the support with the modified analyte and labeled modified analyte, the support is separated from the liquid phase the amount of signal from the solid phase or the liquid phase is then determined, which indicates the extent of binding between the modified analyte and the antibody, and thus the amount of analyte in the sample. For a more detailed discussion of the above immunoassay techniques, see "Enzyme-Immunoassay," by Edward T. Maggio, CRC Press, Inc., Boca Raton, Fla., 1980.

For illustrative purposes, the following assay protocols can be utilized. These illustrations should not be construed as limiting the scope of the invention, but are merely illustrative of the qualitative, semi-quantitative and quantitative assay protocols in which the method of this invention can be used for determining Hcy or Cys in a sample. The signal detected in these methods is compared to a standard or control, having a known concentration of Hcy.

(A) In an assay for Hcy using Modifying Reagent (I), a monoclonal antibody that specifically binds to modified Hcy (Ib) and not to modified Cys (Ia), is utilized. A sample suspected of containing Hcy and Cys is combined with Modifying Reagent (I) inca suitable medium. The reactions will occur as follows: Reagent (I)+Hcy→modified Hcy (Ib)

and Reagent (I)+Cys→modified Cys (Ia), if Hcy and Cys are present. An analog of modified Hcy (Ib), conjugated to glucose-6-phosphate dehydrogenase, is also added to the medium. After enough time has elapsed for the reactions and immunological binding to occur, the anti-Hcy antibody is added to the medium. After incubation for 30 minutes, glucose-6-phosphate is added. The signal produced is directly related to the amount of Hcy in the sample.

(B) In an assay for total Hcy in serum, a monoclonal antibody that specifically binds to modified Hcy (Vb) and not to modified Cys (Va), is utilized. The antibody is bound to glass beads. The serum sample is first treated with dithiothreitol (DTT) to reductively liberate any Hcy tied up as disulfides. Excess DTT is sequestered by treatment with sodium arsenite. The pretreated sample is then combined with Modifying Reagent (V), which has been labeled with $^3$H, and then combined with the glass bead-bound antibody. The medium is incubated for 10 minutes and the beads separated and washed. The radioactivity of the beads is then measured. The signal produced is directly related to the amount of Hcy in the sample.

C) In an assay for Hcy using Modifying Reagent (IX), a monoclonal antibody that specifically binds to modified Hcy (IXb) and not to modified Cys (IXa), is bound to a support. An analog of modified Hcy (IXb), conjugated to horseradish peroxidase (HRP), is also utilized. A sample suspected of containing Hcy and Cys is combined with Modifying Reagent (IX) in a suitable medium. After enough time has elapsed for the reactions to occur, the anti-Hcy-support conjugate and the modified Hcy-HRP conjugate are then added to the medium. After incubation of the suspension for 30 minutes, the liquid and solid phases are separated, and the solid phase washed. An aqueous medium, to which substrate has been added is then added to the solid phase and the signal produced is inversely related to the amount of Hcy in the sample.

The method of this invention further involves the preparation of polyclonal and monoclonal antibodies to immunogens homologous to the immunologically distinct analyte, i.e., the "modified" analyte. The immunogen used to obtain the antibodies useful in the methods of the present invention is the modified analyte, which is obtained by reacting the compound being assayed with the selected modifying reagent. Typically, for preparation of the immunogen, first the solubilizing groups of the modifying reagents are used for attaching the reagent to an immunogenic carrier protein. Usually these attaching groups are first activated and the reagent is then coupled to the carrier protein. The resulting reagent-protein conjugate is then allowed to react with the analyte, purified, and used as an immunogen.

This invention pertains to a method of detecting a first compound in the presence of a second compound, which is a homolog of the first. Therefore, the antibodies described above are screened for their ability to react specifically with the reaction product of the modifying reagent and either the first compound (analyte) or the second compound; i.e., bind to either the modified analyte or to the modified second compound. For example, in an assay for Hcy, the immunogen would be the derivatized Hcy linked to an immunogenic carrier protein. The resulting antibodies would then be capable of specifically recognizing the modified Hcy analyte and would not recognize the modified Cys.

Other groups for attaching the modifying reagent to the protein carrier can be used, including, for example, aldehydes, ketones, diazonium salts, alkylating agents, etc. Conveniently, carboxylic acids or sulfonic acids are converted to active esters or acid halides for conjugation. The carrier protein may be any protein, preferably one that is foreign to the animal being immunized such as keyhole limpet hemocyanin or bovine serum albumin, if the animal is, for example, a mouse, rabbit, sheep or goat.

Preparation of polyclonal antibodies useful in the methods of this invention, is by methods such as are well known in the art. Monoclonal antibodies are essentially obtained by a process similar to that described in Milstein and Kohler, *Nature* 256:495–497 (1975). The details of the Milstein and Kohler process are well established. Generally, the process involves injecting a host, usually a mouse or other suitable animal, with an immunogen. Cells are then taken from the spleen of the animal. Alternatively, the host may be unsensitized spleen cells, which are sensitized to the immunogen in vitro. The resulting cells are fused with myeloma cells. The result is a hybrid cell, referred to as a "hybridoma" that can be cultured in vitro. The population of hybridomas is screened and manipulated so as to isolate individual clones, each of which secretes a single antibody to the antigen.

When the immunogen is introduced into the host, the host's immune system responds by producing a variety of antibodies that are able to recognize various sites on the immunogen. These numerous antibodies have different affinities and specificities. To obtain those antibodies that have desirable affinity and specificity traits for the particular assay method being used, the different hybridoma cell lines are screened.

As a matter of convenience, the reagents for use in the present invention can be provided in a kit for use in an assay method. A typical kit for use in a method for detecting Hcy, comprises in a packaged combination: a modifying reagent capable of chemically modifying Hcy and Cys to form modified Hcy and modified Cys, and an antibody capable of specifically binding to the modified Hcy but not to the modified Cys. The kit can further comprise a labeled analog of the modified Hcy. The kit can also comprise a releasing agent suitable for releasing any Hcy in the disulfide form.

Under appropriate circumstances one or more of the reagents in the kit can be provided in solution or as a dry powder, usually lyophilized, including excipients, which on dissolution will provide for a reagent solution having the appropriate concentrations for performing a method or assay in accordance with the present invention. To enhance the versatility of the subject invention, the reagents can be provided in packaged combination, in the same or separate containers, so that the ratio of the reagents provides for substantial optimization of the method and assay. The reagents may each be in separate containers or various reagents can be combined in one or more containers depending on the cross-reactivity and stability of the reagents. As a matter of convenience, the reagents employed in the present invention can be provided in predetermined amounts. The reagents can include a first antibody and a second antibody, which are capable of specifically binding the modified analyte and a reagent to chemically modify the analyte. The kit can also contain written instructions on how to use the reagents and/or how to perform a particular assay, for example in the form of a package insert.

The invention is demonstrated further by the following illustrative example.

ABBREVIATIONS

AP Alkaline Phosphatase (calf intestinal)
BABA p-Bromoacetylbenzoic Acid
BSA Bovine Serum Albumin
Cys-ABA Cysteine Acetylbenzoic Acid
DCC Dicyclohexylcarbodiimide DPBS Dulbecco's Phosphate Buffered Saline
DTT Dithiothreitol
DMEM Dulbecco's Modified Eagle Medium
DMSO Dimethylsulfoxide
EDTA Ethylenediaminetetraacetic Acid
FBS Fetal Bovine Serum
HCy-ABA Homocysteine Acetylbenzoic Acid
Hcy-ABA-BSA Homocysteine Acetylbenzoic Acid-Bovine Serum Albumin
Hcy-ABA-AP Homocysteine Acetylbenzoic Acid-Alkaline Phosphatase Conjugate
NHS N-Hydroxysuccinimide
PBS Phosphate Buffered Saline
PEG Polyethylene Glycol
PNPP Phenylphosphate
S-DMEM Super Dulbecco's Modified Eagle Medium
RAM Rabbit Anti-Mouse
TCEP Tris(2-carboxyethyl)phosphine
THF Tetrahydrofuran

PREPARATION OF MATERIALS

BSA Cohn crystallized was from ICN. AP was from Pierce. All other chemicals were reagent grade and commercially available from sources such as Gibco and Sigma. All solutions were prepared in $H_2O$ and all reactions were performed under ambient conditions unless otherwise stated.

A) Preparation of p-Bromoacetylbenzoic Acid (mw 243)

2.0 g (12.2 mmole) of 4-acetyl benzoic acid was added to 90 ml of acetic acid in a 500 ml erlenmeyer flask and heated at 45° C. until dissolved. Maintaining the temperature at 45° C., 1.95 g (12.2 mmole, 0.61 ml) of bromine dissolved in ~2 ml acetic acid was added slowly over 1 hour with vigorous stirring. The reaction required an induction period of several minutes before proceeding, which became evident by the loss of the red bromine color and the evolution of HBr. The product, BABA (Modifying Reagent II), was precipitated on ice, collected by filtration and recrystallized 3 times from hot (75° C.) ethanol.

B) Preparation of Bromoacetylbenzoic Acid N-hydroxysuccinamide Ester (mw 340)

BABA was prepared as described above and recrystallized once. To 0.6 g BABA (2.5mmole) and 0.28 g NHS (2.5 mmole) dissolved in 8 ml dry THF at 0° C. was added 0.51 g (2.5 mmole) DCC in 1 ml THF. A precipitate was observed after several minutes and the solution stirred overnight. The solution was filtered through a glass frit and the volume reduced to ~2 ml under vacuum. Some precipitation was observed following volume reduction. An excess of petroleum ether was added to precipitate the remaining product and the solid was recrystallized by dissolving in a limiting amount of THF and adding back petroleum ether until turbid, then cooling to −20° C. and collecting the solid by filtration. Yield of BABA-NHS, 0.2 g.

C) Preparation of Cysteine Acetylbenzoic Acid (mw 283)

60 mg of BABA and 60 mg of 1-cysteine were added to 5.0 ml of 200 mM Na phosphate, pH 7.5, and stirred for 10 minutes, after which 0.5 ml of 1.0M HCl was added to precipitate the product. The solid was collected by filtration, washed with 0.1M HCl and then with water and finally dried under vacuum to yield Cys-ABA (modified Cys IIa). TLC analysis (cellulose, 0.1M ammonium acetate, pH 6.8) and NMR (spectra recorded in $D_2O$ containing 100 mM $Na_2DPO_4$, pH 7.5; 100 mM $NaDCO_3$, pH 8.4; and 100 mM $Na_2B_3O_7$, pH 9.3) showed the presence of at least three different pH dependent products. The mass spectral analysis (CI) produced a parent peak at mw 221 indicative of decarboxylation.

D) Preparation of Homocysteine Acetylbenzoic Acid (mw 297)

100 mg of 1-homocysteine thiolactone was added to 5.0 ml of degassed 0.5M NaOH, heated to 45° C. for 10 minutes and neutralized to pH 8.0 with a combination of 1.0M and concentrated HCl. 80 mg of BABA was added to the Hcy solution and stirred for 15 minutes. The solution was then filtered through a 0.22 micron syringe filter and the solution pH lowered to ~2 by the addition of 1.0M HCl in order to precipitate the product. The solid Hcy-ABA (modified Hcy IIb) was washed several times with 0.1M HCl, collected by centrifugation and dried under vacuum.

E) Preparation of Homocysteine Acetylbenzoic Acid-Bovine Serum Albumin Conjugate 25 mg of BSA was dissolved in 5.0 ml 100 mM Na phosphate, pH 7.0, and 2.2 ml of this solution was added to 200 μof 100 mM BABA–NHS in DMSO (+BABA–NHS rxn) or to 200 μof DMSO alone (–BABA–NHS rxn) and mixed for 3 hours. The two samples were then centrifuged to precipitate the excess solid BABA–NHS, filtered through a 0.45 micron syringe filter and concentrated 5 times on a Centricon 30. The concentrated solutions were diluted to 1.0 ml with 100 mM Na phosphate, pH 7.0. A 20 μaliquot was removed from each solution, diluted to 1.0 ml and the absorbance measured to determine the reaction efficiency. The protein concentration was determined from the –BABA–NHS reaction (BSA, $\epsilon_{280}$=43,600) and the protein-bound BABA concentration from the +BABA–NHS reaction (BABA, $\epsilon_{260}$=13,600).

Hcy was further reacted with the BABA-activated BSA solutions prepared above. 20 mM 1-homocysteine was prepared by dissolving 1.5 mg of 1-homocysteine thiolactone in 0.5 ml 1M NaOH, incubating 10 minutes at 37° C. and finally diluting with 2.0 ml Na phosphate, pH 7.0, and 2.5 ml Na phosphate, pH 6.0 (final pH 7). Both BSA solutions prepared above were diluted to 4.0 ml with $H_2O$ and 1.0 ml of the Hcy solution was added to each and incubated overnight. The reactions were concentrated on a Centricon 30 and the reaction efficiency was estimated from the Br$^-$ concentration of the retained filtrates. Bromide standards were prepared by adding 2 μl of the appropriate KBr stock solutions to 98 μl of the –BABA–NHS reaction filtrate, producing standards with Br$^-$ concentrations of 0.0, 0.2, 0.4, 0.8, and 1.0 mM. 20 μl of the prepared Br$^-$ standards or 20 μl of the filtrate from the +BABA–NHS reaction were added to 0.9 ml of 0.1M Na citrate pH 5.5, followed by 20 μl of 0.8 mM fluorescein and 10 μl of 0.1M chloramine T. After 10 minutes, 20 μl of 25 mM thiosulfate in 0.2M $Na_2CO_3$ was added to stop the reaction and the absorbance recorded for each sample at 515 nm in a 1 cm cell. The absorbance values of the standards were plotted against the Br$^-$ concentrations to produce a standard curve, from which the concentration of Br$^-$ contained in the +BABA–NHS reaction was determined. From this value an estimate was obtained of the coupling efficiency of the BABA groups on BSA with Hcy. The +BABA–NHS reaction solution was concentrated 4 times on a Centricon 30, diluted with 1 ml 1× PBS (final conc. ~10 mg/ml) and set aside for subsequent antibody development.

F) Preparation of Homocysteine Acetylbenzoic Acid-Alkaline Phosphatase Conjugate The Hcy-ABA-AP conjugate was prepared in a similar fashion to the BSA conjugate described above. 10 mg of AP was diluted with 15 ml 100 mM Na phosphate, pH 7.0, and concentrated 3 times on a Centricon 30, after which 200 mM Na phosphate, pH 7.0, was added to a final volume of 2.0 ml. Two reactions were prepared: 0.48 ml of the AP solution was added to 45 µl of 100 mM BABA–NHS in DMSO (+BABA–NHS rxn) or 45 µl of DMSO alone (–BABA–NHS rxn) and the reactions mixed for 2.5 hours. The reactions were then diluted with 2.0 ml H$_2$O, filtered through a 0.45 µl syringe filter, concentrated 5 times on a Centricon 30 and finally diluted to 1.0 ml with 100 mM Na phosphate, pH 7.0. 20 µl of each sample were diluted to 1.0 ml, the absorbance recorded and the ratio of protein-bound BABA to AP determined as before (AP, $\epsilon_{280}$=110,000; BABA, $\epsilon_{260}$=13,600).

The BABA-activated AP was reacted with Hcy as follows. 9.3 mg of 1-homocysteine thiolactone was dissolved in 0.5 ml 1.0M NaOH and incubated for 15 minutes at 37° C. The Hcy was neutralized with 0.5M Na$_2$HPO$_4$ and H$_2$O to a final volume of 5 ml and pH 7.0. 200 µl of the Hcy solution was added to both AP solutions prepared above and incubated for 4 hours at 37° C. The reactions were then concentrated by Centricon 30 and the filtrates retained.

The extent of the coupling reaction of BABA-activated AP with Hcy was estimated from the concentration of Br$^-$ released. Standard solutions were prepared by mixing 2 µl of stock KBr solutions with 98 µl of a buffer resembling the filtrate in composition (1.0 ml of 100 mM Na phosphate 7.0 added to 200 µl 0.5M Hcy) to give standards of 0.0, 0.05, 0.1, 0.15, and 0.2 mM bromide ion. 80 µl of the Br$^-$ standards or the filtrate from the +BABA–NHS rxn was added to 0.9 ml of 0.1M Na citrate, pH 5.5, followed by 40 µl 0.4 mM fluorescein and 30 µl 1 50 mM chloramine T and incubated for 10 minutes. 50 µl of 15 mM thiosulfate in 0.1M Na$_2$CO$_3$ was added to stop the reaction and the absorbance at 515 nm recorded. The Br$^-$ concentration contained in the +BABA–NHS rxn filtrate was determined from the standard curve and used to estimate the efficiency of the reaction with Hcy. Both the –BABA–NHS and +BABA–NHS reactions were concentrated 5 times on a Centricon 30 and 1×PBS added back to a final volume of 400 µl.

The activity of derivatized AP was evaluated by diluting 2 µl of each AP solution in 100 µl H$_2$O and adding 2 µl of the diluted solution to 1.0 ml of 1 mg/ml PNPP in 50 mM Tris Cl, pH 9.4, and comparing the change in absorbance recorded over 30 seconds.

G) Production and Isolation of Hcy-ABA-BSA Monoclonal Antibodies

1) Immunogens, Immunizations, and Enzyme-Conjugates

The Hcy-ABA-BSA immunogen was prepared as described above. Mice were immunized intraperitoneally once with 100 µg and twice with 50 µg of immunogen emulsified in RIBI Adjuvant System. Three days prior to the fusion, mice received a saline boost intraperitoneally containing 250 µg of immunogen.

Hcy-ABA-AP was used for screening.

2) Tissue Culture

S-DMEM was used for all tissue culture, which consisted of DMEM supplemented with:

10% FBS

10% NCTC-135 (Gibco #440-1100EC)

4 mM glutamine 1 mM oxaloacetic acid 1 mM sodium pyruvate 0.148 nM L-cysteine 200 units insulin 37.9 mM sodium bicarbonate Conditioned media was prepared by growing P388D1 cells (ATCC TIB 63) in S-DMEM and splitting 1:4 every four to five days. Spent media was centrifuged at 1500 rpm for 15 minutes. The spent media was then filtered using a 0.2 micron sterile tissue culture filter unit to remove any remaining cells and debris. Glutamine (100×stock=58.5 µg/L) was added to the spent media before using or freezing at –20° C. for future use. Conditioned S-DMEM was prepared by supplementing S-DMEM with 10% P38D1 spent media and then using it to support hybridoma growth after fusion and during cloning.

Mouse myeloma cell line P3X63 Ag8.653 (Ag8.653, ATCC CRL 1580) was maintained in culture by splitting 1:2 to 1:4 daily or by serial dilution in a 6-well plate for two days.

3) Fusions

Fusions were done essentially according to the procedure of Milstein and Kohler, *Nature* 256:495–497 (1975).

Spleen were aseptically removed from two immunized mice and placed in a 60 mm tissue culture dish containing 10 mL DMEM. They were minced a few times and then mashed between the ends of two frosted slides. A single cell suspension of splenocytes was attained by passing the cell suspension through a monofilament screen cloth. The splenocytes, about 2×10$^8$ cells, were combined with 40×10$^6$ Ag8.653 cells, centrifuged at 800 rpm for 5 minutes, and washed 1 to 2 times with DMEM. Fusion was performed by addition of 4.0 mL PEG (50% solution in 75 mM Hepes), which was added over 3 minutes while gently stirring, and then 30 to 40 mL S-DMEM was added to inactivate the PEG. The cell suspension was centrifuged at 800 rpm for 5 minutes. Supernatant was poured off, and the cells were resuspended with 240 mL S-DMEM-HAT (stock HAT=50× Sigma #H0262; in media: 100 µM hypoxanthine, 0.4 µM aminopterin, and 16 µM thymidine) and plated at 200 µL/well into twelve 96-well culture plates.

Cells were fed by removal of 100 µL/well of spent media and subsequent addition of 200 µL/well of conditioned S-DMEM-HAT 4 to 5 days after the fusion.

Fusions were screened about 7 to 10 days after the fusion. Hybridoma colonies were usually then visible by eye while the media was still pink or just turning yellow.

4) Cloning by Serial Dilution

Hybridomas producing ELISA positive antibodies were then cloned several times by serial dilution to ensure single cell colonies. The procedure was as follows.

Contents from a well,of a 96-well plate were transferred to a well in a 24-well plate containing 1.5 mL/well of conditioned S-DMEM. Cells were mixed by pipetting, and 100 µL/well were added to the first row of a 96-well plate containing 200 µL/well conditioned S-DMEM. One hundred µL/well were transferred to the second row using a Flow Multichannel pipettor, mixed by pipetting, and again 100 µL/well were transferred to the next row. Each "clone" was serially diluted 7 times, 1 to 4 clones per plate. Cells were recloned by limiting dilution 3 to 4 times or until stable.

5) Freezing and Thawing Cell Lines

Cloned and stabilized cell lines that were ELISA+ were stored at –100° C. The chosen well (clone) from a 96-well plate was grown up by daily passaging of cells and sequentially expanding from a 24-well plate with 1.5 mL/well S-DMEM, next into a 6-well plate with 8 mL/well S-DMEM, and finally into a T-75 flask with 50 mL S-DMEM.

Cells from a T-75 flask were centrifuged at 800 rpm for 5 minutes and resuspended in 3 mL of freezing medium, 10% DMSO (ATCC #76-68-5) and an additional 10% FBS in S-DMEM. One-mL (3 to 5×10$^6$ cells) aliquots were pipetted into cryovials, which were then placed in a freezing container. The container was then stored at –100° C. for 1–2 days, and then the vials were transferred to a −100° C. freezer storage box for later use.

Cells were thawed by warming the vials in a 37° C. water bath. The cell suspension was transferred to a 15-mL centrifuge tube containing 5 mL of S-DMEM and then centrifuged at 800 rpm for 5 minutes. The supernatant was decanted and the cells resuspended in 8 mL of S-DMEM and pipetted into a 6-well plate for cell expansion.

6) Screening

The hybridomas were initially screened by the competitive reverse ELISA screen, then later screened by reverse ELISA. All ELISA screens were performed at room temperature. The competitive reverse ELISA protocol was used for primary screens using only one concentration of Hcy-ABA, the modified form of Hcy, to identify antibodies. To identify the best antibodies, the competitive reverse ELISA was performed using Hcy-ABA at two different levels to determine relative sensitivity of the antibodies. BABA and Cys-ABA were also used to determine if there was any undesirable cross reactivity. The reverse ELISA protocol was used for subsequent screens of cloning plates. The reagents for the competitive reverse ELISA and the reverse ELISA were:

DPBS (10X), pH 7.4, diluted 1:10

50 mM Carbonate Buffer, pH 9.0

ELISA Wash Buffer: 0.5% Tween 20 in DPBS

Plate coat: Rabbit anti-Mouse IgG, A, M; heavy & light (Zymed), reconstituted with 2 mL water per manufacturer's instructions, diluted 1:100 in DPBS (RAM)

Plate block: 1% BSA in DPBS

Diluent: 0.5% BSA in DPBS; diluted plate block 1:2 in DPBS

ELISA enzyme-ligand conjugates: AP-Hcy-ABA, diluted 1:1500 in diluent; competitive reverse ELISA: for primary screen, Hcy-ABA was diluted to 0.8 µg/mL in diluted Hcy-ABA-AP; for characterization of antibodies, Hcy-ABA, Cys-ABA and BABA were diluted to 1 µg/mL and 1 ng/mn of diluted APHcy-ABA in carbonate buffer.

Substrate buffer: 1M diethanolamine, 0.25 mM $MgCl_2$, pH 9.8

Substrate: 0.25 mg p-nitrophenyl phosphate per mL of substrate buffer

The protocol for competitive reverse ELISA and reverse ELISA was:

1. Plates were coated with RAM, 50 µL/well, incubated one hour or up to one week at 4° C., and then the contents of the wells were emptied.
2. Plates were blocked with 300 µL/well, incubated 15 minutes and then the contents of the wells were emptied.
3. Antibody (spent media) was added, 50 µL/well, incubated 45 minutes, and washed 3 times.
4. Competitive reverse ELISA: 50 µL/well of AP-Hcy-ABA or AP-Hcy-ABA plus Hcy-ABA, AP-Hcy-ABA plus Cys-ABA, or Hcy-ABA-AP plus BABA were added to replicate plates. Reverse ELISA: 50 µL/well of AP-HCy-ABA was added. Plates were incubated 45 minutes, and washed 3 times.
5. Substrate was added, 100 µL/well, incubated on a shaker for 20 to 30 minutes and read at 405 nm.
6. Positives in the primary screen were antibodies with ODs greater than 0.9 with, AP-Hcy-ABA only and better than 50% competition with Hcy-ABA-AP +Hcy-ABA. Percent competition was computed as:

$$\% \text{ Competition} = \frac{OD \text{ w/AP-Hcy-ABA} - OD \text{ w/AP-Hcy-ABA and Hcy-ABA}}{OD \text{ w/AP-Hcy-ABA}} \times 100$$

Positives from screening cloning plates using the reverse ELISA protocol were the wells with a single colony or fewest colonies with an elevated OD.

7) Production and Purification of In Vitro Antibody ELISA positive hybridomas that were cloned and stabilized were then expanded in static culture. Hybridomas were overgrown to two-T225 flasks (500 mL of spent media) or to four-T225 flasks (1-L of spent media). Cells and debris were separated by centrifugation and filtration. Sodium azide was added at 0.02% before purification. Antibodies produced in static culture were purified by Protein G column chromatography. Purification was performed at room temperature. Reagents used for Protein G purification were:

Washing/binding buffer, PBS pH 7.0: 0.01M sodium phosphate, 0.15M sodium chloride, and 0.02% sodium azide Elution buffer: 0.5M acetic acid adjusted to pH 3.0 with ammonium hydroxide Neutralizing solution: 1M tris base Cleaning buffer: 1M acetic acid The protocol used for Protein G purification was:

1. A column was packed with 10 mL of Protein G and washed with 25 mL of washing/binding buffer.
2. Antibody (spent media), 0.5 to 1-L, was loaded onto the column.
3. The column was washed with washing/binding buffer until OD returned to baseline or with about 50 mL.
4. Antibody was eluted with elution buffer. Two mL were collected per fraction into a test tube already containing 1 mL of neutralizing solution.
5. The antibody peak was pooled and dialyzed overnight against 4-L DPBS, pH 7.4.
6. The column was washed with about 25 mL of cleaning buffer and then re-equilibrated with the washing/binding buffer.

7. Antibody purity was checked by Paragon electrophoresis for presence of a single band. Antibody concentration was determined by first getting an OD of the antibody solution at 280 nm, then calculating antibody concentration using the extinction coefficient for IgG: $As_{280}$ (1 mg/mn)= 1.35.

Results: Competitive reverse ELISA data showed thirteen antibodies that competed well with Hcy-ABA, and competed poorly, if at all, with Cys-ABA or BABA. Sensitivity at 1 µg/mL of Hcy-ABA was very good. Antibodies from the clone designated Hcy I 5C12 were selected for use in the following experiment.

H) Preparation of Biotin Hyc I 5C12

400 µl of the 0.7 mg/ml antibody solution (Hcy I 5C12) was concentrated 2 times on a Centricon 30 diluting with 100 mM Na carbonate, pH 8.5. The solution was filtered and buffer added to a volume of 300 µl (final conc. ~1 mg/ml). To the antibody solution was added 36 µl of 1 mg/ml biotinamido-caproate-NHS ester in DMSO and incubated for 2 hours. The reaction was concentrated 5 times on a Centricon 30, finally adding back 50 mM Na phosphate, pH 7.5, to a final volume of 1 ml. The concentration of antibody (100 µg/ml) was determined from the 280 nm absorbance (1.2 mg/ml→abs. of 1.0). Successful biotinylation was verified by Paragon gel electrophoresis by comparing the mobility of the unmodified and biotinylated antibody in the absence and presence of streptavidin. The biotin-Hcy I 5C12 solution was finally concentrated to a volume of 50 μl on a Centricon 30.

EXAMPLE I

HPLC HOMOCYSTEINE ASSAY WITH DTT-ARSENITE REDUCTION

To 200 μl samples of whole blood, coagulation halted with EDTA, were added aliquots of 1.0 mM Hcy to give final concentrations of 0, 10, 20, 30, 40 μM. The blood was incubated for 2 hours at room temperature, then stored for 3 days at 4° C. to allow for equilibration between the free-reduced, free-disulfide and protein-bound forms of Hcy. 20 μl of plasma obtained from each blood sample was reduced by adding 10 μl 100 mM DTT and 30 μl 1.0M Na carbonate, pH 8.2, and incubating at 37° C. for 30 minutes. The proteins in the sample were subsequently removed by filtration through a Millipore Ultrafree MC (10K MW cutoff). Excess DTT was sequestered by adding 10 μl 1.0M Na arsenite to 20 μl of the filtrate and incubating for 10 minutes. 10 μl of 10 mM BABA was added and the reaction incubated for an additional 10 minutes. The derivatized plasma samples were then analyzed by HPLC and. the Hcy-ABA peak quantitated, allowing for accurate determination of total plasma Hcy. (20 μl injection, 1.0 ml/min, 10 cm Alltech Econosphere C18 column, gradient: 1–10% CH₃CN in100 mM Et₃N-HOAc, pH 5.5, over 15 minutes). The data fit well to a linear least squares analysis. If extrapolated to zero area the plasma-alone sample registered ~28 mM Hcy, a value larger than expected (~12M is normal). However the Hcy concentration in stored blood has been shown to increase substantially over time.

EXAMPLE II

HPLC HOMOCYSTEINE ANALYSIS OF PLASMA WITH AND WITHOUT TCEP REDUCTION

TCEP at low mM concentrations was shown to quantitatively reduce Hcy in buffer. To show that TCEP was also effective at reducing disulfides in plasma, plasma-alone (no Hcy) was reacted with BABA with or without prior reduction with TCEP. 20 μl of plasma was added to 30 μl of 1.0M Na bicarbonate and 10 μl of H₂O or 10 μl of 20 mM TCEP and incubated at 37° C. for 5 minutes:

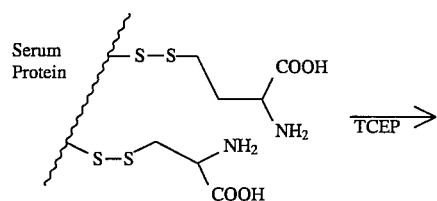

-continued

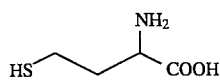

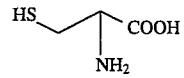

60 μl of 10 mM BABA was then added and the reaction incubated for 5 minutes:

Proteins were removed by filtration as above and the reactions analyzed for Hcy-ABA by HPLC (conditions as above except; gradient: 1–20% CH₃CN in 1% trifluoroacetic acid over 15 minutes). No product was observed unless TCEP was present. HPLC analysis also indicated that the Hcy-ABA peak was not completely resolved from other compounds and the experiment must be viewed in qualitative terms as evidence that reduction with TCEP will effect disulfide reduction in plasma (or serum).

EXAMPLE III Hcy-ABA INHIBITION OF Hcy-ABA-AP BINDING TO BIOTIN-Hcy I 5C12

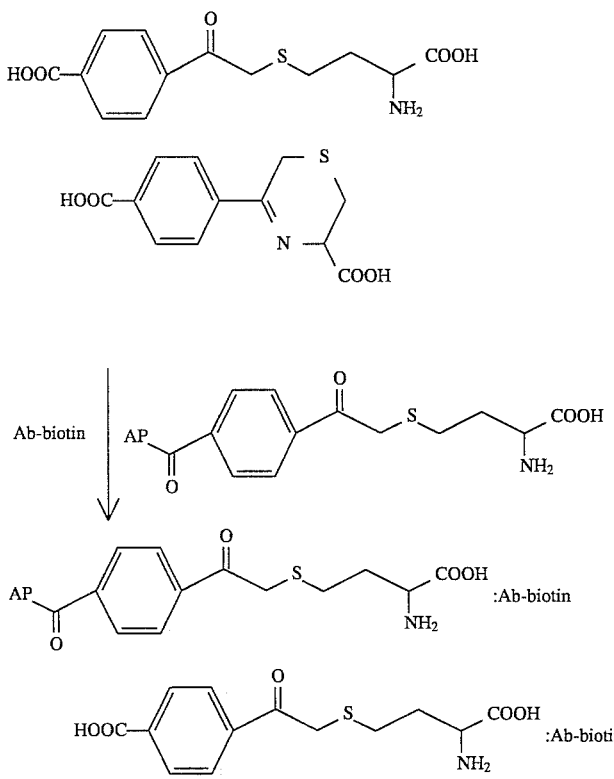

100 µl of 1×PBS, 0.05% Tween containing 5 ng of Hcy-ABA-AP was added to 100 µl of H₂O containing Hcy-ABA at a concentration of 0.125, 0.25, 0.5, 1.0 or 4.0 µM. 100 µl of PBS-Tween containing 10 ng biotin-Hcy I 5C12 was added and the reaction incubated for 20 minutes. Prewashed streptavidin-coated particles (1 pellet) were suspended in 300 µl PBS-Tween and 20 µl was added to the reaction. The reaction tube was agitated for 15 minutes such that the particles remained suspended. The particles were then washed 5 times with PBS-Tween, the separation of the particles from solution being facilitated by pulling the particles to the side with a tube holder containing a magnetic strip. 300 µl of 1 mg/ml PNPP substrate in 50 mM Tris Cl, pH 9.3, was added and mixed for 20 minutes. 200 µl of solution from each reaction tube was transferred to a microtiter plate and the absorbance recorded at 414 nm on a plate reader. As expected, an increase in the concentration of Hcy-ABA caused a diminution in the magnitude of the recorded absorbance. Signal modulation was >50% over an effective solution concentration range of 0.04 to 0.67 mM (no zero concentration data point was recorded), allowing for a substantial dilution of serum sample (typical Hcy concentration ~12 mM), while still maintaining an adequate sensitivity level in the immunoassay.

EXAMPLE IV

ASSAY OF HOMOCYSTEINE-SPIKED SERUM

Serum samples were spiked with 10, 20, 30 and 40 µM Hcy (added as Hcy, i.e., the dimeric form of Hcy). Six reactions were prepared in which 5 µl of each Hcy-spiked serum sample or serum alone (two reactions) was reduced by adding 10 µl of 1.0M Na phosphate, pH 7.5, and 10 µl of 10 mM TCEP and incubating for 10 minutes. The resulting free Hcy in 5 samples was derivatized, i.e., "modified" by adding 40 µl of 8 mM BABA and incubating for 10 minutes. To one of the "serum alone" samples, BABA was replaced by adding bromoacetamide, creating a zero Hcy-ABA control. 40 µl of BABA (1 sample) or bromoacetamide (5 samples) was then added to balance the reagent mix, followed successively by 100 µl PBS-Tween containing 10 ng Hcy-ABA-AP and 100 µl PBS-Tween containing 20 ng biotin-HCy I 5C12 and incubation for 15 minutes. 20 µl of a streptavidin-coated particle suspension was added and the reaction agitated for 15 minutes. After washing 5 times with PBS-Tween the reaction was developed with PNPP and analyzed as described above. The data points were fitted to a smooth curve in a plot of added Hcy versus the recorded absorbance. The absorbance reading from the serum-alone, bromoacetamide derivatized sample was fitted to the curve and the endogenous Hcy concentration of the serum-alone sample (0 mM added Hcy) was estimated by comparison with the zero Hcy-ABA (+bromoacetamide) control. From the graph the Hcy concentration of the serum sample was 15 µM, a value that is within the expected range for a normal individual.

Although the foregoing invention has been described in some detail by way of illustration and example for the purposes of clarity and understanding, it will be obvious that certain changes or modifications may be practiced within the scope of the appended claims.

What is claimed is:

1. A method of determining the amount of homocysteine in the presence of cysteine in a sample suspected of containing said homocysteine, comprising the steps of:
   (a) bringing together in an aqueous medium:
      (1) said sample,
      (2) a modifying reagent capable of chemically modifying homocysteine and cysteine to form modified homocysteine and modified cysteine, and (3) an antibody capable of specifically binding to said modified homocysteine but not to said modified cysteine to form an immunecomplex; and (b) measuring the amount of said immunecomplex, the amount thereof being related to the amount of homocysteine in said sample.

2. The method of claim 1 wherein said modifying reagent modifies the sulfhydryl groups of said homocysteine and said cysteine to form a modified homocysteine where the sulfur is not part of a ring, and a modified cysteine where the sulfur is part of a ring.

3. The method of claim 1 wherein said modifying reagent is selected from the group consisting of alkylating agents, acylating agents and metals.

4. The method of claim 1 wherein said modifying reagent has a detectable label, and said label is detected to measure the amount of said immunecomplex.

5. The method of claim 4 wherein said antibody is bound to a support or is capable of being bound to a support.

6. The method of claim 1 wherein said antibody is detectably labeled or is capable of being detectably labeled and said label is detected to measure the amount of said immunecomplex.

7. The method of claim 1 which further comprises bringing together an analog of said modified homocysteine bound to a detectable label, wherein said antibody is also capable of specifically binding to said analog to form a second immunecomplex, wherein the amount of said first immunecomplex is measured by measuring the amount of said second immunecomplex.

8. The method of claim 7 wherein said antibody is bound to a support or is capable of being bound to a support.

9. A method of determining the amount of homocysteine in the presence of cysteine in a sample suspected of containing said homocysteine, comprising the steps of:

(a) bringing together in an aqueous medium:
(1) said sample,
(2) a modifying reagent capable of chemically modifying homocysteine and cysteine to form modified homocysteine and modified cysteine,
(3) an analog of said modified homocysteine bound to a detectable label, and
(4) an antibody capable of specifically binding to said modified homocysteine and to said analog, but not to said modified cysteine; and (b) measuring the immunecomplex formed by the binding of said analog to said antibody, the amount thereof being related to the amount of homocysteine in said sample.

10. The method of claim 9 wherein said modifying reagent is selected from the group consisting of alkylating agents, acylating agents and metals.

11. The method of claim 9 wherein said antibody is bound to a support or is capable of being bound to a support.

12. The method of claim 11 which further comprises bringing together a support bound to a first specific binding pair member and said antibody is bound to a complementary second specific binding pair member.

13. The method of claim 9 wherein said label is selected from the group consisting of fluorescers, radiolabels, enzymes, chemiluminescers and photosensitizers.

14. The method of claim 9 wherein said antibody is bound to a first member of a signal producing system and said detectable label is a second member of a signal producing system, and the amount of said immunecomplex is measured by detecting the signal produced by the interaction of said signal producing system members.

15. A method of determining the amount of homocysteine in a sample suspected of containing homocysteine and cysteine, comprising the steps of:

(a) bringing together in an aqueous medium:
(1) said sample,
(2) a modifying reagent capable of chemically modifying homocysteine and cysteine to form modified homocysteine and modified cysteine,
(3) an antibody capable of specifically binding to said modified homocysteine but not to said modified cysteine to form a first immunecomplex,
(4) a surface capable of binding said antibody, and
(5) a labeled analog of said modified homocysteine that is capable of binding said antibody to form a second immunecomplex; and (b) measuring the amount of said second immunecomplex, the amount thereof being related to the amount of homocysteine in said sample.

16. The method of claim 15 wherein said modifying reagent is selected from the group consisting of alkylating agents, acylating agents and metals.

17. The method of claim 15 wherein the label of said labeled analog is selected from the group consisting of fluorescers, radiolabels, enzymes, chemiluminescers and photosensitizers.

18. The method of claim 15 which further comprises bringing together a labeled first specific binding pair member, wherein the label of said labeled analog is a complementary second specific binding pair member.

19. A method of determining the amount of homocysteine in a sample suspected of containing homocysteine and cysteine, comprising the steps of:

(a) bringing together in an aqueous medium:
(1) said sample,
(2) a modifying reagent capable of chemically modifying homocysteine and cysteine to form modified homocysteine and modified cysteine,
(3) an antibody capable of specifically binding to said modified homocysteine but not to said modified cysteine to form an immunecomplex, and
(4) a receptor capable of binding to a portion of said modifying reagent, wherein said portion is present on said modified homocysteine;

(b) measuring the amount of said immunecomplex, the amount thereof being related to the amount of homocysteine in said sample.

20. The method of claim 19 wherein said portion of said modifying reagent is selected from the group consisting of haptens, biotin and fluorescein; and said receptor is selected from the group consisting of antibodies, avidin and streptavidin.

21. A method of determining the amount of homocysteine in the presence of cysteine in a serum sample suspected of containing said homocysteine, wherein at least a portion of said homocysteine is in the disulfide form (protein-bound and free-disulfide), comprising the steps of:

(a) bringing together in an aqueous medium:
(1) said sample
(2) a releasing agent to release said homocysteine from the disulfide form,
(3) a modifying reagent capable of chemically modifying the sulfhydryl groups of homocysteine and cysteine to form modified homocysteine and modified cysteine, and
(4) an antibody capable of specifically binding to said modified homocysteine but not to said modified cysteine to form an immunecomplex;

(b) examining said medium for the amount of said immunecomplex, the amount thereof being related to the amount of homocysteine in said sample.

22. The method of claim 21 wherein chemically modifying said sulfhydryl group of cysteine comprises the formation of a six-membered ring.

23. The method of claim 22 wherein chemically modifying said sulfhydryl group of homocysteine does not comprise the formation of a six-membered ring.

24. The method of claim 21 wherein the releasing agent is a reducing agent.

25. The method of claim 21 wherein said modifying reagent is a ketone substituted at the alpha position by a leaving group selected from the group consisting of Cl, Br, I, sulfonates, and sulfonium salts.

26. The method of claim 21 wherein the amount of said immunecomplex is determined by detection of enzyme activity, luminescence, light absorbance or radioactivity.

27. A kit for use in a method for detecting homocysteine, comprising in a packaged combination:

a modifying reagent capable of chemically modifying homocysteine and cysteine to form modified homocysteine and modified cysteine, and an antibody capable of specifically binding to said modified homocysteine but not to said modified cysteine.

28. The kit of claim 27 which further comprises a labeled analog of said modified homocysteine.

29. The kit of claim 27 which further comprises a releasing agent to release any homocysteine present in a disulfide form.

* * * * *